(12) United States Patent
Pawlowicz et al.

(10) Patent No.: US 9,529,040 B2
(45) Date of Patent: *Dec. 27, 2016

(54) CIRCUIT TRACING USING A FOCUSED ION BEAM

(71) Applicant: TECHINSIGHTS INC., Ottawa (CA)

(72) Inventors: Christopher Pawlowicz, Ottawa (CA); Alexander Sorkin, Nepean (CA); Alexander Krechmer, Ottawa (CA)

(73) Assignee: TECHINSIGHTS INC., Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/811,549

(22) Filed: Jul. 28, 2015

(65) Prior Publication Data

US 2016/0187419 A1    Jun. 30, 2016

Related U.S. Application Data

(63) Continuation-in-part of application No. 14/309,674, filed on Jun. 19, 2014, now Pat. No. 9,383,327, which
(Continued)

(51) Int. Cl.
*G21G 5/00* (2006.01)
*G01R 31/303* (2006.01)
(Continued)

(52) U.S. Cl.
CPC ......... *G01R 31/303* (2013.01); *G01N 23/2255* (2013.01); *G01R 31/2896* (2013.01);
(Continued)

(58) Field of Classification Search
CPC .............. H01J 2237/28; H01J 2237/244; H01J 2237/2516; H01J 2237/2806; H01J 37/26; H01J 37/3006; G01N 23/2251; G01N 27/60; G01R 31/307
(Continued)

(56) References Cited

U.S. PATENT DOCUMENTS

8,791,436 B1    7/2014  Pawlowicz et al.
2008/0237487 A1  10/2008  Pinto et al.
(Continued)

*Primary Examiner* — Nicole Ippolito
*Assistant Examiner* — Hanway Chang
(74) *Attorney, Agent, or Firm* — Knobbe, Martens, Olson & Bear, LLP (57) ABSTRACT

Described are various embodiments of methods and systems for tracing circuitry on integrated circuits using focused ion beam based imaging techniques. In one such embodiment, a method is provide for identifying functional componentry associated with a switchable power interface on an integrated circuit, wherein the switchable power interface comprises a source and a drain with a control switch therebetween, said control switch being controllable by a control signal during operation of the integrated circuit. The method comprises connecting, with deposited conductive material, the source and the drain; applying an external voltage bias to a power input of the switchable power interface via one of the source and the drain; exposing the integrated circuit to a focused ion beam; and gathering an image of the integrated circuit during exposure to determine areas of high contrast indicating functional componentry in operative connection with the switchable power interface.

25 Claims, 6 Drawing Sheets

Related U.S. Application Data is a continuation of application No. 13/869,749, filed on Apr. 24, 2013, now Pat. No. 8,791,436.

(51) Int. Cl.
*G01R 31/28* (2006.01)
*G01N 23/225* (2006.01)
*H01L 21/66* (2006.01)

(52) U.S. Cl.
CPC .... *H01L 22/12* (2013.01); *H01J 2237/24564* (2013.01); *H01J 2237/24585* (2013.01); *H01J 2237/2803* (2013.01); *H01J 2237/2809* (2013.01); *H01J 2237/31749* (2013.01)

(58) Field of Classification Search
USPC .......... 250/306, 307, 309, 311, 492.1, 492.2, 250/492.21, 492.3
See application file for complete search history.

(56) References Cited

U.S. PATENT DOCUMENTS

2010/0038555 A1    2/2010   Tsao
2014/0319343 A1   10/2014   Pawlowicz et al.

CIRCUIT TRACING USING A FOCUSED ION BEAM

FIELD OF THE DISCLOSURE

The present disclosure relates to circuit tracing, and in particular, to circuit tracing using a focused ion beam.

BACKGROUND

The technological revolution of the late 20th and early 21st century has put a premium on competitive corporate intelligence. Companies, especially those involved in high tech, seek to determine what their competitors are putting in their latest products. To this end, integrated circuits, especially high value, cutting edge, microchips are constantly being reverse engineered, analyzed, and dissected to determine what are their internal structures and interconnections.

Currently, the dissection and analysis of integrated circuits involves a painstaking, laborious process. Each layer in a multi-layer microchip is carefully exposed and imaged/photographed. A mosaic of the images is then created and the traces are then laboriously traced to determine which feature is interconnected with which component. As can be imagined, this resource-intensive process can lead to mistakes as features and areas which may not be of interest may need to be imaged and analyzed, simply to ensure that the features of interest are covered.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

A need exists for circuit tracing systems and methods that overcome some of the drawbacks of known techniques, or at least, provide a useful alternative thereto. Some aspects of this disclosure provide examples of such systems and methods.

A further or alternative need exists for systems, methods, and devices which can reduce the effort required to trace circuits and interconnects on integrated circuits, for example.

In accordance with some aspects, there are provided methods and systems for tracing circuitry on integrated circuits using focused ion beam based imaging techniques. In one such aspect, a first component or node on an integrated circuit is coupled to a second component or node on the same integrated circuit. An external bias is then applied to the first component or node. A focused ion beam is applied to the integrated circuit and an image is taken using an electron detector. The features or components on the integrated circuit which are coupled to the second component or node will show up in high contrast on the resulting image. The method can be used in an iterative process to identify which components are coupled to which features on the integrated circuit. The method may also involve applying a bias to a node or component and then using focused ion beam imaging techniques (through an electron detector) to arrive at an image of the integrated circuit. Other components or nodes coupled to the node or component to which the bias was applied will appear in high contrast on the resulting image.

In accordance with one exemplary embodiment, a method for imaging circuitry on an integrated circuit is provided comprising: coupling a first part of said integrated circuit with a second part of said integrated circuit; applying a bias voltage to said first part; exposing said integrated circuit to a focused ion beam; and gathering an image of said integrated circuit using an electron detector; wherein said first part and said second part are not coupled through said integrated circuit; and wherein said image gathered has at least one portion in high contrast compared to a rest of said image, said at least one portion being a portion of said integrated circuit which is coupled to said second part of said integrated circuit.

In accordance with another exemplary embodiment, a method is provided for tracing interconnections in an integrated circuit, the method comprising: removing layers of said integrated circuit to expose components of said integrated circuit; coupling a first node of said integrated circuit to a second node of said integrated circuit; applying an external bias voltage to said first node; capturing an image of at least a portion of said integrated circuit using a focused ion beam and an electron detector; determining which components of said integrated circuit are illustrated in high contrast in said image; wherein, prior to said coupling, said first node and second node are not coupled to one another through said integrated circuit.

In accordance with another exemplary embodiment, a method is provided for imaging circuitry on an integrated circuit, the method comprising: applying an external electrical bias on to a first portion of said integrated circuit; exposing said integrated circuit to a focused ion beam; gathering an image of said integrated circuit; wherein said image gathered shows a second portion of said integrated circuit which is in high contrast compared to a rest of said image, said first and second portions being interconnected through a common path in said integrated circuit.

In accordance with another exemplary embodiment, a method is provided for identifying functional componentry associated with a switchable power interface on an integrated circuit, wherein the switchable power interface comprises a source and a drain with a control switch therebetween, said control switch being controllable by a control signal during operation of the integrated circuit, the method comprising: connecting, with deposited conductive material, the source and the drain; applying an external voltage bias to a power input of the switchable power interface via one of the source and the drain; exposing the integrated circuit to a focused ion beam; and gathering an image of the integrated circuit during exposure to determine areas of high contrast indicating functional componentry in operative connection with the switchable power interface.

In accordance with another exemplary embodiment, a method is provided a method for identifying distinctly powered functional blocks on an integrated circuit, each of the functional blocks powered via respective power interfaces of a switchable power interface on the integrated circuit, the method comprising: applying an external voltage bias to the switchable power interface; imaging the integrated circuit using a focused ion beam; identifying imaged components exhibiting high contrast as representative of the respective power interfaces; conductively closing a selected one of the identified imaged components; imaging the integrated circuit using said focused ion beam; and identifying an area of high contrast as representative of a given one of the distinctly powered functional blocks as being operatively powered via said selected one of the respective power interfaces.

In accordance with another exemplary embodiment, a method is provided a method for identifying distinctly powered functional blocks on an integrated circuit, each of the functional blocks powered via respective power interfaces of a switchable power interface on the integrated circuit, the method comprising: identifying the respective power interfaces; conductively closing a selected one of the respective power interfaces; applying an external voltage bias to the switchable power interface; imaging the integrated circuit using a focused ion beam; and identifying an area of high contrast as representative of a given one of the distinctly powered functional blocks as being operatively powered via said selected one of the respective power interfaces.

In accordance with another exemplary embodiment, a method is provided a method for identifying a switchable power interface on an integrated circuit, wherein the switchable power interface comprises a source and a drain with a control switch therebetween, the control switch being controllable by a control signal during operation of the integrated circuit, the method comprising: applying an external voltage bias to a power input on the integrated circuit; gathering an image of the integrated circuit when exposed to an ion beam; and identifying an endpoint of an area of high contrast indicating conductive connectivity with said power input, said endpoint identifying the switchable power interface having the source and the drain.

In accordance with another exemplary embodiment, a method is provided a device for identifying distinctly powered functional blocks on an integrated circuit, each of the functional blocks powered via respective power interfaces of a switchable power interface on the integrated circuit, the device comprising: a focused ion beam emitter for directing an ion beam at a substrate; a secondary electron detector for measuring at each of a plurality of locations on the substrate respective intensities of secondary electrons emitted from the substrate when exposed to the ion beam, each said measured intensity for generating image data indicative of features at each said respective location; and a bias applicator for connecting an external voltage bias to a portion of the integrated circuit conductively associated with said switchable power interface; wherein differences in regions of high contrast in respective images of said integrated circuit taken before and after shorting said switchable power interface indicate a distinctly powered functional block on said integrated circuit.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

DETAILED DESCRIPTION

The systems and methods described herein provide, in accordance with different embodiments, different examples of circuit tracing methods and systems using a focused ion beam.

Focused Ion Beam (FIB) systems are well established in the semiconductor industry and come in a variety of configurations for a number of different uses. In FIB systems, a focused beam is generated and the beam is accelerated down a column. The beam is then manipulated by applying electromagnetic energy through a system of coils (and electrostatic lenses), and the resulting beam emerges in a vacuum chamber and strikes a sample/target. For FIB, the beam consists of ions as ion beams have much more kinetic energy than electron beams. By striking a sample with high power, material can be milled away and removed. By adding background gas and striking the sample with lower energy, new material can be deposited. By manipulating the beam and adding a gas, one can deposit and remove material in a precise and controlled manner. Standard gases which may be used include xenon difluoride, tetramethylcyclotetrasiloxane (TMCTS), platinum, tungsten, and other well-known gases.

After the ion beam strikes a sample, ions, atoms and electrons are emitted (mostly 'secondary electrons'). These electrons can be used to create an image—an image can be obtained by using an electron detector and synchronizing the collected signal with the ion beam scanning. Depending on the sample's materials and other factors, more or less electrons might be emitted. The image can therefore be used to identify regions of the sample with different characteristics. As an example, metal circuitry will emit a different number of electrons than dielectric areas and this causes metal circuitry to appear different than dielectric areas in the image.

Figure 1:
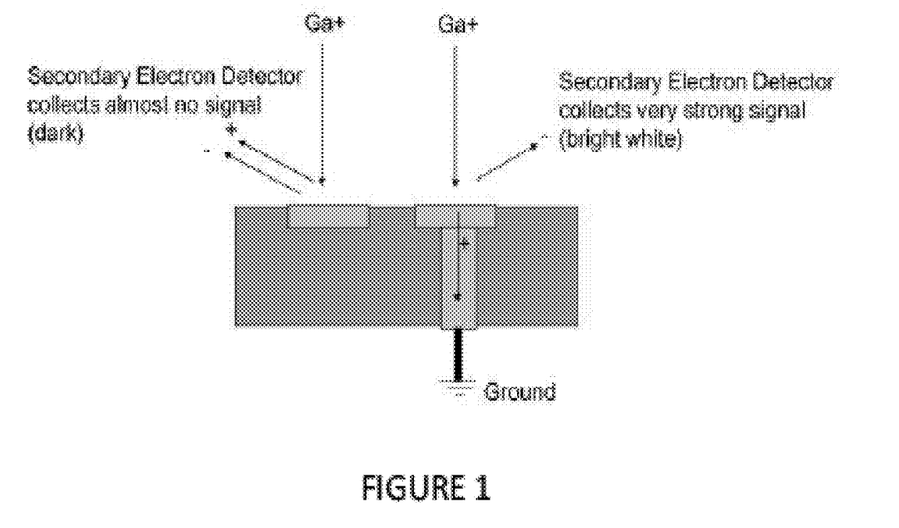
FIGS. 1 and 2 are schematic diagrams provided to explain focused ion beam (FIB) technology, in accordance with one embodiment.

Referring to FIG. 1, a schematic view explaining focused ion beam technology is illustrated. As can be seen in FIG. 1, a focused ion beam (from a gallium ion source) is applied to a sample. The ion beam causes electrons to be emitted by the sample. These electrons are detected by a secondary electron detector. From the emitted electrons, an image of the sample can be constructed. As can also be seen in FIG. 1, by grounding one of the features of the sample and thereby rerouting positive particles, a brighter image can be obtained for the grounded feature. This is because the secondary electron detector receives a higher concentration of electrons compared to the ungrounded feature.

A well known phenomenon occurs when an ion beam strikes an area of semiconductor with embedded dopant material. Since N-doped silicon behaves differently from P-doped silicon when struck by an ion beam, the resulting image shows contrast differences between the materials. Materials other than semiconductors also show this behaviour, known as voltage contrast, in various degrees.

Figure 2:
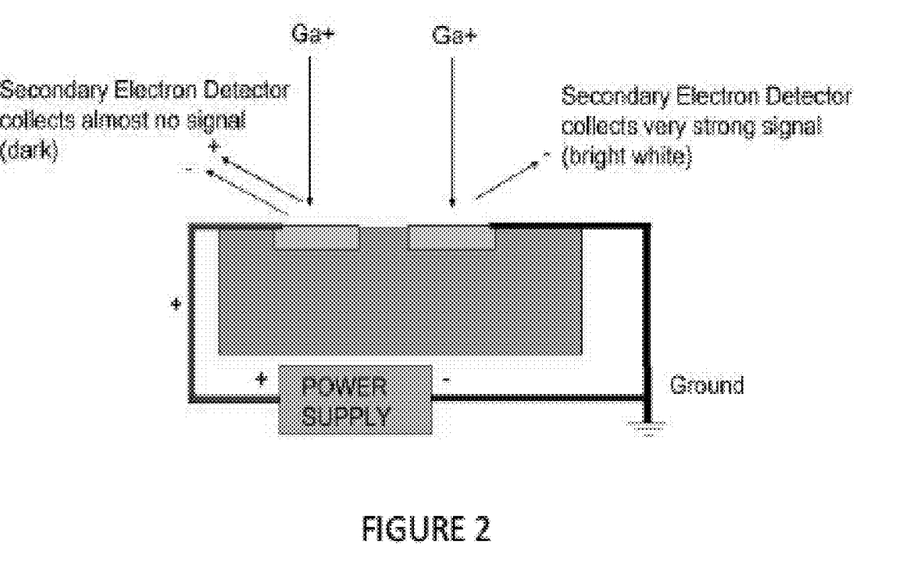

By way of explanation, FIG. 2 is provided. In this Figure, two features on an integrated circuit (IC) are coupled by means of an electrical circuit. When a focused ion beam is applied to the features, the feature on the IC which is coupled to ground produces a brighter image. Again, this is because the secondary electron detector receives a higher concentration of electrons from the grounded feature as compared to the ungrounded feature.

Figure 3:
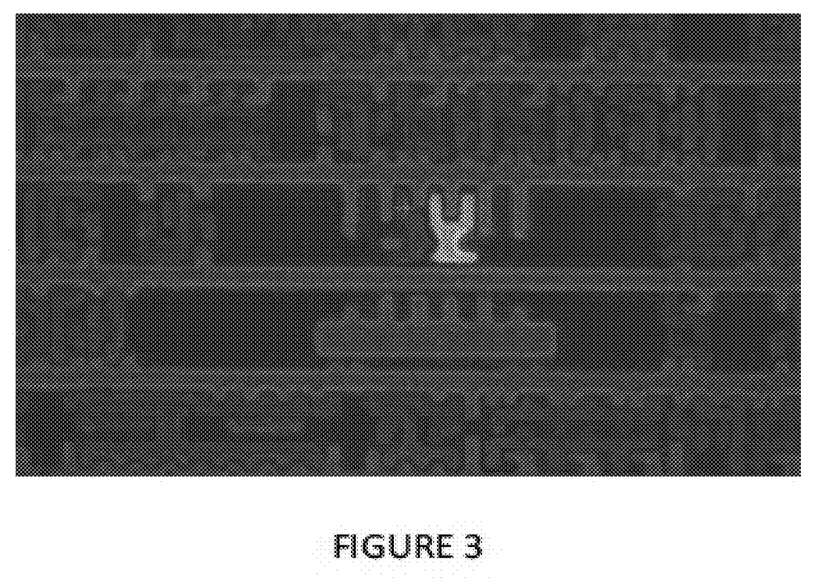
FIG. 3 is an image derived from FIB illustrating a feature of an IC in high contrast, in accordance with one embodiment.

Extending the concept explained by FIG. 2, a focused ion beam can be used to strike a sample which has a mixture of dielectric material and metal interconnect (e.g. a delayered IC die). By making external connections to specific areas of circuitry and applying a bias voltage to those areas, the amount of electrons generated when these areas are struck by an ion beam can be made to vary greatly. Using this technique, specific areas of the integrated circuit can be made to show much higher brightness (i.e. higher contrast) in the resulting image as compared to other areas when plotting the secondary electron yield. One example of this is shown in FIG. 3 where an IC feature/component has been biased and an FIB has been applied. As can be seen, the feature to which a bias has been applied is in high contrast to the rest of the IC.

The high brightness (or high contrast) area can be extended by using normal circuit-edit FIB manipulation. By depositing dielectric material, milling access holes, and depositing metal interconnect, the biased area can be connected to a new area or a new component or node of the IC. Any areas, components, or nodes coupled to the biased area will, when struck by a focused ion beam, similarly appear in high contrast in the resulting image derived from the secondary electron detector output. This can be used to determine which features, nodes, or components on an IC are connected to which areas, features, nodes, or components.

Figure 3A:
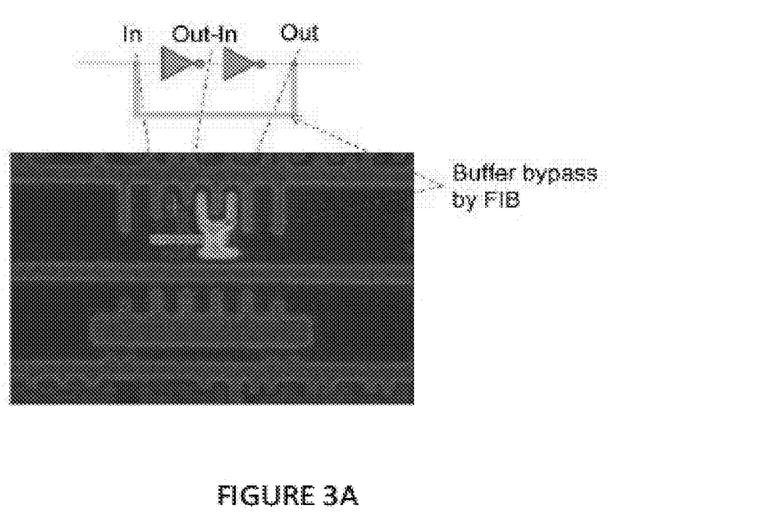
FIG. 3A is a schematic diagram with an image from FIB showing the coupling between two features on an IC, in accordance with one embodiment.

Referring to FIGS. 3A-6, the steps in the coupling between a known feature and an unknown area or feature in the IC is illustrated. FIG. 3A shows, in a schematic diagram, the 20 desired end result for shorting two features on the IC. As can be seen, a known feature (the buffer feature in high contrast) is to be shorted with an adjacent feature, also a buffer. The yellow block between the highlighted buffer component and its adjacent buffer represents a short that couples these buffers to one another in FIG. 3A.

Figure 4:
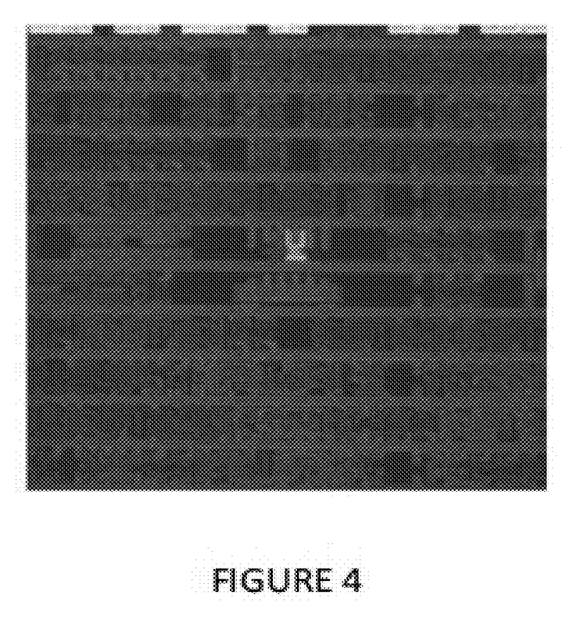
FIG. 4 is an image of a feature in high contrast using FIB, in accordance with one embodiment.
Figure 5:
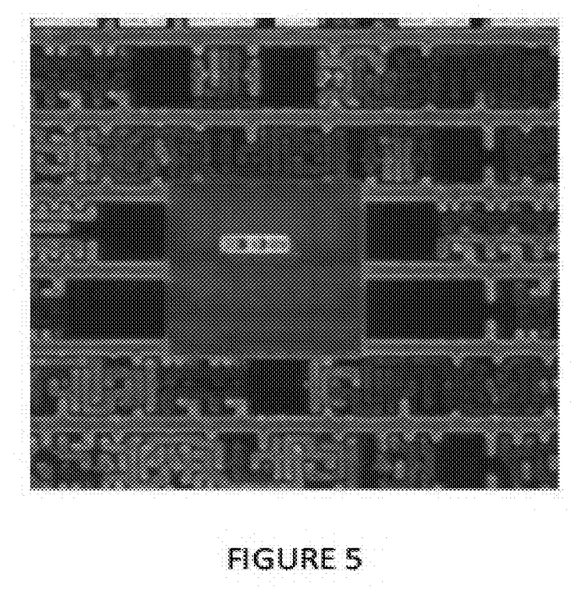
FIG. 5 is an image of the feature in FIG. 4 with a dielectric patch deposited, in accordance with one embodiment.
Figure 6:
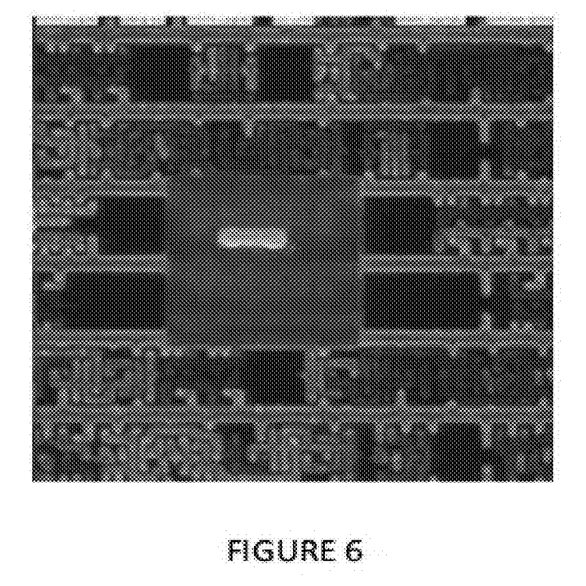
FIG. 6 is an image of the feature in FIG. 4 with the nodes of the known feature and of the unknown feature being shorted, in accordance with one embodiment.

In FIG. 4, the known feature (a buffer) is biased and the FIB derived image shows the feature in high contrast relative to the other features on the IC. In FIG. 5, a dielectric patch is deposited on the known feature and the nodes of the known feature and an unknown feature (i.e. a non-biased feature) are exposed. In FIG. 6, the nodes of the known feature and of the unknown feature are shorted by depositing conductor material between the two nodes. Once shorted, the two nodes are thus coupled and applying a bias to the shorted nodes has the effect of applying a bias to whatever nodes, features, or components are coupled to the unknown feature. When a focused ion beam is thus applied to the IC while the bias is being applied, these nodes, features, or components coupled to the unknown feature will also appear in high (or higher) contrast when compared to the unbiased parts or areas of the IC.

Figure 7:
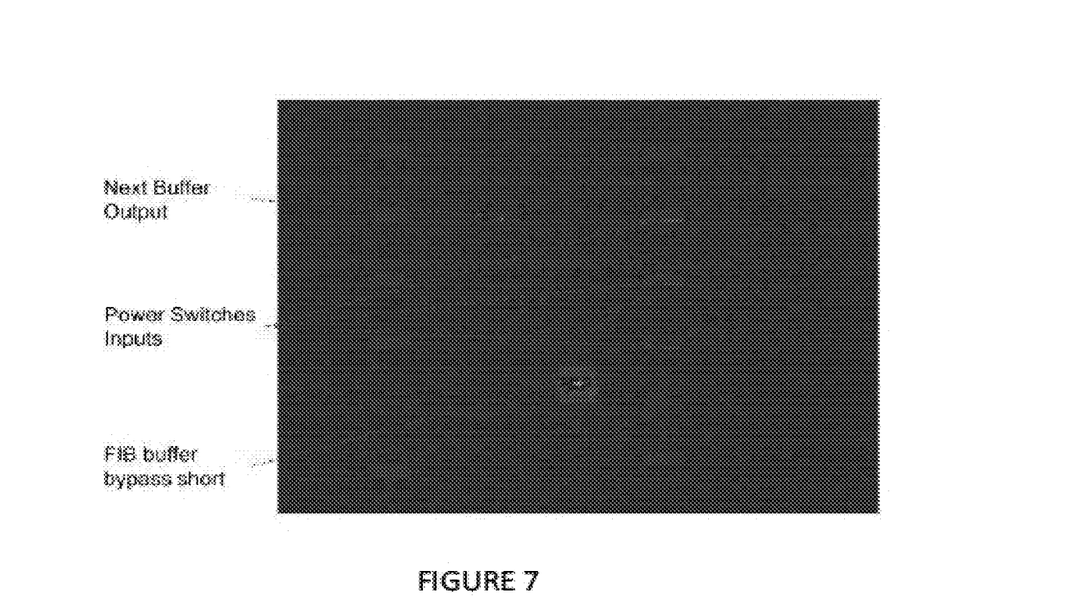
FIG. 7 is an image of the integrated circuit of FIG. 6 showing the different parts of the IC being in high contrast due to the bias being applied to the known feature, in accordance with one embodiment.

Referring to FIG. 7, the shorted area (i.e. the area to which a bias has been applied) is illustrated in the lower middle part of the image. The features of the IC which are coupled to the unknown feature appear in higher contrast than the rest of the IC. As can be seen in FIG. 7, these features include inputs to the power switches as well as an output for the next buffer.

It should be noted that the example given in FIGS. 3A-7 should not be taken as being limiting to the present disclosure. Any feature, node, or component on an integrated circuit or microchip can be used as a first or initial component or node. This first component can then be shorted or coupled with a second component by any appropriate means prior to applying a bias and a focused ion beam to the integrated circuit. While the example given uses FIB to deposit and remove dielectric as well as metal interconnect, other techniques may be used. Also, while the example uses a gallium ion source for the focused ion beam, other ion sources, such as elemental gold, iridium, xenon, neon, as well any other suitable ion sources, may be used.

It should also be noted that, for best results, the first and second nodes or components which are to be coupled to each other are preferably not coupled to one another by way of the integrated circuit prior to being coupled to one another for biasing and imaging purposes.

In one implementation, to work one aspect of the present disclosure, an integrated circuit chip or die is first prepared using standard known back-side sample preparation methods. This involves mounting the die to an insulating carrier face-down, then removing the die bulk silicon using wet or dry etching until the gate level components are exposed. The die can be further processed from the back using standard techniques to expose the specific layer of interest. One approach would be to expose the Metal 1 level. Once the level or component of interest has been exposed, a signal path is extended from an external source to the node, component, or feature of interest. A bias voltage is applied to the signal node or feature, typically using an external power supply.

After applying the bias voltage, the sample is then placed inside a focused ion beam chamber. The chamber is then pumped with a vacuum pump, and the sample is exposed to a FIB beam. By varying the beam conditions, the imaging detector conditions, and the external bias voltage, the signal node can be made to show up with very high contrast compared to the rest of the circuitry in the Secondary Electron (SE) imaging detector image. The node or feature of interest can be made to appear illuminated while the rest of the circuitry is dark.

Once the feature of interest has been biased and been made to appear in high contrast, the high contrast area can be extended. Using the ability of the focused ion beam technique to deposit insulating material and conducting material very precisely, the signal path is extended to a new section or feature of circuitry. In the case of a single transistor, the original biasing signal might be applied to one node of a transistor (e.g. a gate, source or drain contact) and, using focused ion beam deposition techniques, the biasing signal can be extended to another node of the transistor (e.g. gate, source or drain contact). Once the bias signal has been extended to the new feature, any other nodes connected to that node will appear illuminated in the SE image.

It should be noted that, while the signal path may extend invisibly through many metal layers (more than 10 on a modern IC), wherever it is connected to another metal 1 area will be instantly visible in the SE image.

Once the new connected node has been revealed, the procedure can be repeated and the next node can thus be illuminated. By continuing to traverse the circuit and form these connections, the circuit can be followed across the IC die. As can be imagined, for circuits involving a number of transistors, this process simply involves the deposition of conductor to short the source contact to the drain contact as well as the application of a bias voltage prior to applying the focused ion beam to the sample.

It should be noted that one aspect of the present disclosure may take the form of simply applying an external bias to a component or node prior to applying a focused ion beam to the integrated circuit. After applying the focused ion beam, an image is taken using an electron detector. The features or components on the integrated circuit which are coupled to the component or node to which the bias was applied will show up in high contrast on the resulting image. The method can be used to identify nodes or components interconnected through a common path on the integrated circuit.

The technique outlined above can be applied to gate level circuitry, contact level circuitry, or any desired metal level (such as Metal 1).

It should be noted that the images obtained using the above outlined process may be further processed to glean further information from the images. As an example, image enhancement techniques may be applied to digital versions of the images derived from the above process to further clarify components, nodes, and features on the IC.

It should further be noted that the images gathered in multiple iterations of the process may be used to determine which features have been highlighted by the application of a bias to relevant part or parts of the integrated circuit. As an example, an image for iteration A (prior to applying a bias to a shorted part of the IC) may be compared to the image for iteration A+1 (subsequent to the application of the bias) to see which parts of the IC have been highlighted. Image subtraction, image manipulation, as well as image addition techniques may be used to automate the process by which the highlighted or highly contrasted parts of the image are determined.

Regarding the conditions and settings for the focused ion beam, various parameters may be adjusted and/or set for optimum resulting image quality. These parameters include voltage, current, dwell time, as well as other parameters. Such parameters and their effects and settings are well known to those versed in the art of focused ion beam techniques. For the electron detector, parameters which may be adjusted to obtain a suitable image quality include, among others, brightness, contrast, and line averaging.

The bias applied to the features of interest may range from +24V+ to −24V. The bias may depend on the focused ion beam conditions as well as the characteristics of the IC being imaged. As examples, the characteristics of the IC may include pattern density, conductor line width/resistance, dielectric quality and conductor quality. Preferably, bias current will be limited to prevent arcing between conductors. The bias current is thus preferably in the microampere range.

Figure 8:
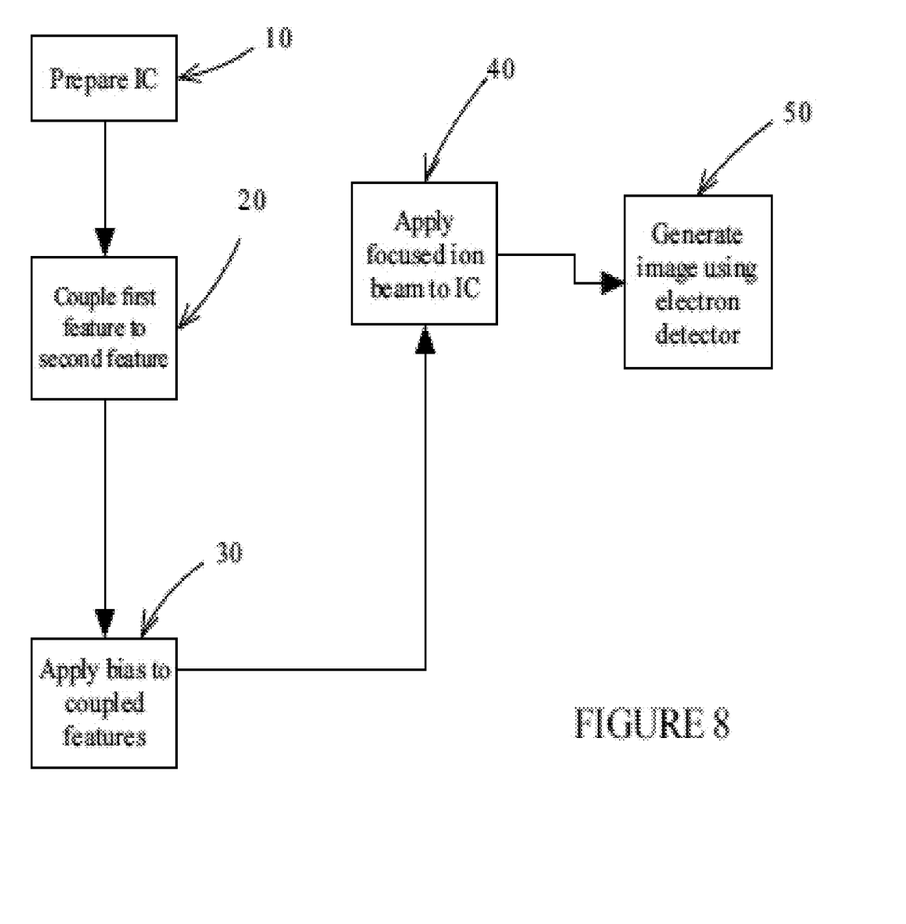
FIG. 8 is a flowchart detailing the steps in a method according to one exemplary embodiment.

One aspect of the present disclosure may be seen as a process detailed by the flowchart in FIG. 8. The process begins at step 10, that of preparing the IC. As noted above, this step may involve exposing the components in the IC to the gate level. Step 20 is that of coupling one feature or node to another. This may be done using different techniques including FIB dielectric deposition. Once a known feature has been coupled to an unknown feature (i.e. a feature whose interconnections are not known), a bias can then be applied to the coupled features (step 30). A focused ion beam can now be applied to the IC (step 40). An electron detector can then be used to generate an image of the IC (step 50). The IC features attached to the biased nodes or features will thus be in high contrast in the resulting image.

In another aspect, there are provided methods and systems to analyze power distribution on an IC at the die level, and associated power distribution of components and subcomponents connected thereto. Such aspects may include simulation of the power switches associated with functional blocks and/or componentry on ICs, and then using the circuit tracing techniques described above to trace the functional block (or componentry), which is activated by such power switches, and determine the location thereof. In aspects, there may be provided an external bias connected to at least one of the power input interfaces and/or power signal interfaces (e.g. leads, pins, pads) on the package or IC die bumps to recognize the power signal propagation on the IC using FIB scanning and imaging. After power switches are identified, their switching function can be simulated by shorting the source and drain of said switches, which may be, for example, Power Switch Transistors (PST).

In modern ICs, power efficiency and management of the power consumption of the IC, and specific componentry thereon, is of particular interest, especially when the IC works in mobile applications, often in smaller devices; when analyzing such devices without prior knowledge of the layout or structures thereof (e.g. when conducting reverse engineering), it is preferable to be able to determine functional componentry associated with a given power switch transistor to better understand important functionality. Because of the known leakage phenomena known to affect transistors on an IC, which may not even be in use, there remains a material consumption of current by such inactive transistors (or other componentry) caused by that passive leakage effect. In order to achieve "smart" or programmable power consumption, the power to specific aspects or subcomponents on an IC may be controlled individually for multiple IC's functional blocks; in some cases, functional blocks are completely disconnected by PSTs whenever the functional block is in idle mode. Internal or external power control circuit is controlling the PST when such functional blocks need to be on or off.

In an exemplary aspect, one or more power input interfaces, including single or groups of leads, pads, or bumps, are identified on an IC package or die level (e.g. Metal 1). Such identification may be provided in advance by a user, or by automated recognition provided by specialized software adapted to compare surface or other substrate geometries to predetermined geometries or characteristics indicating the presence of such interfaces. In some aspects, the identification is preceded by an iterative removal of bulk materials in a layer by layer fashion, wherein features at each layer are analyzed, in part for connectivity to other parts on the same or adjacent layers; in some cases, such analysis is not undertaken, possibly because the size, complexity, or feature density would make such analysis difficult or impracticable. In some aspects, a FIB-based analysis described above for identifying connected circuitry is utilized to identify regions of interest in a given IC.

After identifying the power interface features (i.e. the power group), a first power group is then exposed to an external bias while performing a FIB scanning on the IC die where bulk silicon was removed and transistor layer is exposed. Using the FIB passive voltage contrast (PVC) phenomena permitting the collection of images wherein areas conductively coupled to the application of the external bias are shown in the image with a high contrast relative to other areas. Investigating the high contrast regions one can identify whether the power connected directly to transistors in any given functional block or if the power is connected via one or more PSTs, which are use to switch power transmission to the applicable functional block on or off. PSTs may be associated with an endpoint on a given circuit associated with a transistor; in many cases, a given transistor at such an endpoint is relatively large as compared to other functional transistors since they must be large enough to handle power transmission for a plurality of other transistors or functional componentry. As such, such endpoint transistors are often easily identifiable as PSTs once they have been identified by way FIB scanning and imaging. Thus, the functional blocks that can be switched on or off, and their respective association with specific PSTs can be identified.

After PSTs are identified, simulation of PST functionality can be performed. Using FIB circuit modification capability, conductive material deposition is performed to, in some aspects, connecting or shorting source and drain nodes of one or more of the identified PSTs. Thusly, operation of the given PST can be simulated in that the PST may be opened or closed by a control signal, thus causing power for the PST to be received from power control circuit block. Then, using FIB scanning the power signal propagation will be identified by the high contrast signal which will continue from the shorted by FIB PSTs toward one or more functional blocks. Using the FIB scanning and imaging technique described above, each of the IC's functional block can be investigated in terms of their power supplies, then a correlation between multiple IC's blocks and multiple power supplies can be identified as well.

When one or more PSTs are identified, the control signal which is connected to a gate node of the PST can be traced back using a focused ion beam along with a secondary electron detector for generating an image of the substrate on which the PSTs are located. The PST control signal will be traced back toward the power control circuit block.

In an exemplary aspect, processing cores of some multi-core processors can be turned on and off independently by a switchable power interface, such as a PST. Each core may also be associated directly and indirectly with various other components in an IC. Determining which core (or other componentry or functional blocks) is turned on for given different functionalities and workloads, as well as which components and component-types may be turned on at different times or operating conditions, is also useful. This may be the case when there is little or no pre-existing knowledge of the operation of a processor or other components in an IC. Such cases may exist, for example, when evaluating, comparing, or benchmarking ICs (or other devices); when conducting market or technical intelligence about third-party devices; or when investigating for third-party infringement of intellectual property. The methods disclosed herein may be used in association with reverse engineering.

In another aspect, there is disclosed a method of identifying componentry that is configured to act as a switch for providing power to other componentry in an integrated circuit (or other circuit-based substrate, such as printed circuit board). As a preliminary matter, an external voltage bias is applied to a power input on such an IC, or other substrate, in order to identify one or more endpoints comprising a component on any connected circuit, which will be shown in high-contrast when imaged by the secondary particle detector during exposure of the IC (or other substrate) by an ion beam. Such components located at the endpoint of such a circuit, preferably when such components are transistors, and even more preferably when such transistors are relatively larger than surrounding transistors that are capable of transmitting relatively higher magnitudes of power than such surrounding transistors, such components will typically be a switchable power interface. In many cases, such switchable power interfaces will be a power switch transistor (PST). In normal operation, the PST can be selectively controlled to transmit power, or not transmit power, to functional blocks connected thereto. By turning off power transmission to transistors, or other components, in connected function blocks, loss of power through leakage can be avoided. Since determining which functional blocks are associated with a given PST can be painstakingly difficult, if not impossible, by tracing all circuitry in an IC and working backwards through compiled images at high resolution, the instantly disclosed subject matter provides a way of both identifying the location of such PSTs, but also which functional blocks are associated therewith. For example, there are provided in some aspects methods for identifying switchable power interfaces on an integrated circuit. Said methods, wherein said switchable power interface comprises a source and a drain with a control switch therebetween, said control switch being controllable by a control signal during operation of the integrated circuit, comprise the following: applying an external voltage bias to a power input on an integrated circuit; gathering an image of said integrated circuit when exposed to an ion beam; and identifying an endpoint of an area of high contrast indicating conductive connectivity with said power input, said endpoint comprising an electronic component having a source and a drain.

In some aspects, once a switchable power interface has been identified, the switching mechanism in such switchable power interface may be connected (in other words, shorted) to fix the switch in a closed functionality, thus simulating the state of the switchable power interface when switched into a closed state during operation of the IC. By comparing images of the IC (or other substrate containing conductive elements such as circuitry) before and after such connection, the functional componentry that is turned on, or provided power, by the switchable power interface can be identified. A number of ways of connecting (or shorting) the switch in the switchable power interface known to persons skilled in the art may be used, including but not limited to manual application of conductive material, deposition using lithography, or through deposition by the same or a different focused ion beam. In cases where the switchable power interface is a PST, the PST can be shorted by applying conductive material in contact with both the source and the drain of the PST. For example, there are provided methods which further comprise the step of gathering an additional or second image of the integrated circuit after the step of connecting, and comparing images from before and after.

The areas of high contrast shown solely in the second image will indicate functional componentry in operative connection with said switchable power interface.

In another aspect, there are provided methods for identifying functional blocks associated with a switchable power interface. These may include, but are not restricted to, instances in which the switchable power interfaces have been identified in advance. As such, the functional componentry associated with a given switchable power interface can be determined by, first, connecting, or shorting, the switchable power interface and then exposing the IC (or other substrate) to an ion beam and collecting image data (i.e. the intensity of secondary electrons or other particles as measured by the secondary particle detector), and then by identifying any areas of high contrast associated with the switchable power interface. For example, there is provided a method for identifying functional componentry associated with a switchable power interface on an integrated circuit, wherein said switchable power interface comprises a source and a drain with a control switch therebetween, said control switch being controllable by a control signal during operation of the integrated circuit, the method comprising connecting, with deposited conductive material, the source and the drain, applying an external voltage bias to a power input of said switchable power interface via one of said source and said drain, exposing said integrated circuit to a focused ion beam, and gathering an image of said integrated circuit during exposure to determine areas of high contrast indicating functional componentry in operative connection with said switchable power interface.

In another aspect, the above-described methods, applicable for when a switchable power interface has been identified in advance, may be implemented subsequent to a first image taken for comparison purposes prior to the shorting of the source and drain of the switchable power interface. Such first image, when compared to the final image, will provide a basis for identifying the functional blocks that are provided power by the switchable power interface since, prior to being shorted in a closed position, the associated functional componentry will not be shown in high contrast.

Figure 9A:
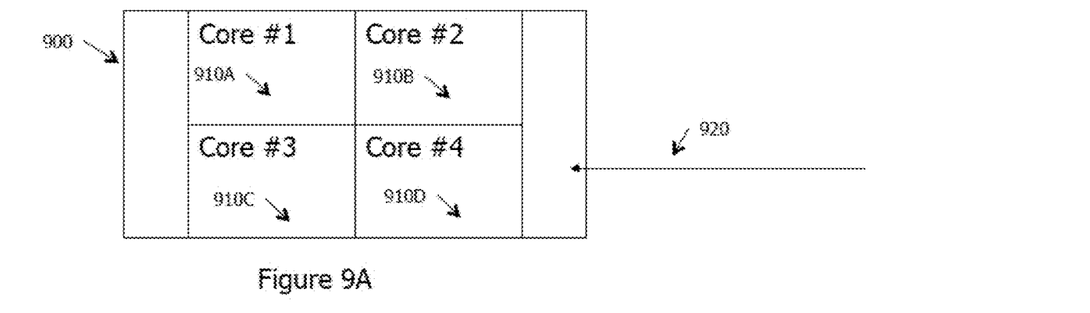
FIG. 9A is a representative diagram of a multi-core processor with no external bias applied.
Figure 9B:
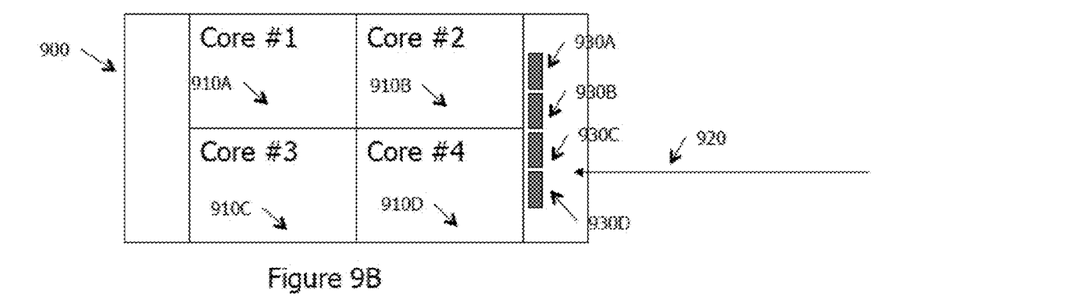
FIG. 9B is a representative diagram of the multi-core processor of FIG. 9A with an external bias applied, in accordance with one embodiment.
Figure 9C:
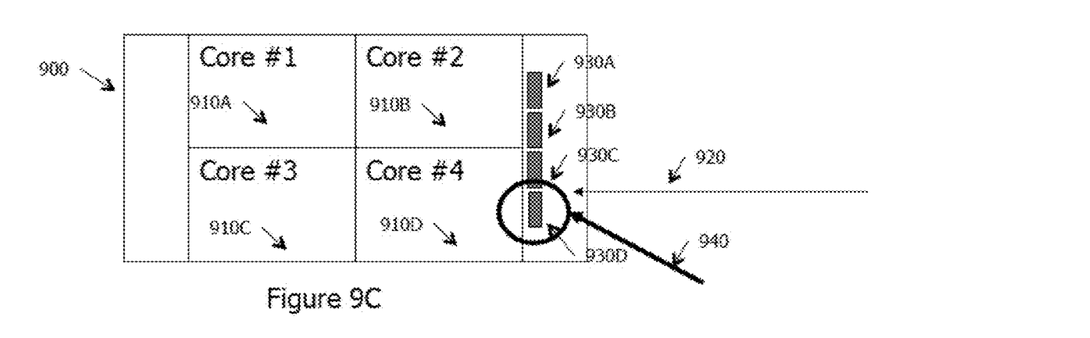
FIG. 9C is a representative diagram of the multi-core processor of FIG. 9A with an external bias applied and an indicator of a deposition of conductive material at a first power switch transistor, in accordance with one embodiment.
Figure 9D:
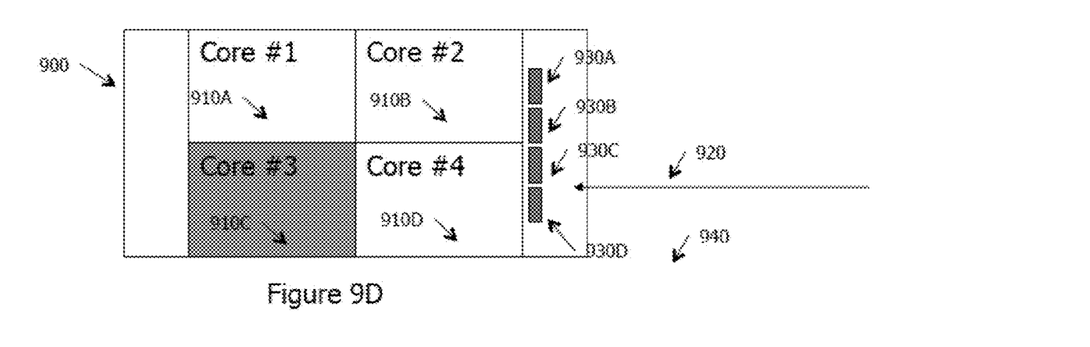
FIG. 9D is a representative diagram of the multi-core processor of FIG. 9A with an external bias applied and a processor core associated with the shorted first power switch transistor shown in high contrast relative to other processor cores, in accordance with one embodiment.

Referring to FIGS. 9A through 9D, there is shown a die that is a multi-core processor 900. In this exemplary aspect, the multi-core processor comprises four cores 910A, 910B, 910C and 910D. In FIG. 9A, no external bias is applied to the external power pin 920 and, as such, no endpoint components are visible. In FIG. 9B, the same die 900 is shown, except an external voltage bias has been applied via the external power pin 920. In this state, the banks of power switching transistors 930A, 930B, 930C and 930D are visible in the associated image. Power switching transistors 930A, 930B, 930C and 930D are in parallel formation with respect to the external power pin. FIG. 9C shows the same die 900, with an external voltage bias applied via the external power pin 920. In this FIG. 9C, a deposition of conductive material has been used to connect, or short, the source and drain of one of the power switching transistors 930D, as shown by deposition indicator 940; in this case, the focused ion beam was used to deposit such conductive material. The resulting image of die 900, as shown in FIG. 9D, once power switching transistor 930D is simulated as if in normal operation with its switch closed, the specific core associated therewith 910C is identified in the resulting image as the functional block with a high contrast relative to other areas (and/or the same area in prior images). The method illustrated by the example in FIGS. 9A through 9D can be iteratively repeated for every identified power switching transistor on a given IC (or other substrate having conductive features, such as a printed circuit board) in order to identify all functional componentries associated with any or all of the power switching transistors. As such, for example, it becomes possible to analyse a single functional block of interest without having to analyze all the circuitry in an integrated circuit in order to assess the connectivity thereto: the methods disclosed herein provide a significant short-cut to determining functional componentry associated with any given power switching transistor and vice versa.

In embodiments, there are provided devices for identifying one or more functional blocks associated with a switchable power interface, particularly such functional blocks that are independently provided power by respective power switching transistors. The device comprises a focused ion beam device for emitting a focused beam of ions in a very controlled manner towards a substrate. The emission of secondary electrons, or other particles, such as other ions, can be measured by a secondary particle detector. The intensity of such detection is indicative of the amount of secondary particles emitted from a given location, wherein an application of an external voltage bias will significantly increase such intensity relative to other features on the substrate. As such, such regions will be shown as areas of high contrast relative to features that are not conductively associated, via a circuit or other conductive material, to the external voltage bias. The device may comprise a voltage applicator, such as wire or other conductor, to apply the external voltage bias to a portion of the substrate (such as a pin, pad or bump on an IC). Lastly, the device may further comprise a deposition tool for depositing conductive material in a controllable fashion, including through the use of the focused ion beam.

While the present disclosure describes various exemplary embodiments, the disclosure is not so limited. To the contrary, the disclosure is intended to cover various modifications and equivalent arrangements included within the general scope of the present disclosure.

What is claimed is:

1. A method for identifying functional componentry associated with a switchable power interface on an integrated circuit, wherein the switchable power interface comprises a source and a drain with a control switch therebetween, said control switch being controllable by a control signal during operation of the integrated circuit, the method comprising:
   connecting, with deposited conductive material, the source and the drain;
   applying an external voltage bias to a power input of the switchable power interface via one of the source and the drain;
   exposing the integrated circuit to a focused ion beam; and
   gathering an image of the integrated circuit during exposure to determine areas of high contrast indicating functional componentry in operative connection with the switchable power interface.

2. The method of claim 1, wherein the switchable power interface is a power switch transistor.

3. The method of claim 1, wherein the functional componentry comprises one or more functional transistors.

4. The method of claim 1, wherein the functional componentry comprises at least a portion of a processing core in a multi-core processor.

5. The method of claim 1, wherein the deposited conductive material is deposited by said focused ion beam.

6. The method of claim 1, wherein a prior image of the integrated circuit is gathered with a prior external voltage bias applied to the power input prior to the step of connecting the source and the drain, said prior image for comparing to the image in isolating said areas of high contrast.

7. A method for identifying distinctly powered functional blocks on an integrated circuit, each of the functional blocks powered via respective power interfaces of a switchable power interface on the integrated circuit, the method comprising:
applying an external voltage bias to the switchable power interface;
imaging the integrated circuit using a focused ion beam;
identifying imaged components exhibiting high contrast as representative of the respective power interfaces;
conductively closing a selected one of the identified imaged components;
imaging the integrated circuit using said focused ion beam; and
identifying an area of high contrast as representative of a given one of the distinctly powered functional blocks as being operatively powered via said selected one of the respective power interfaces.

8. The method of claim 7, wherein said imaged components consist of power switch transistors, and wherein said conductively closing comprises shorting a selected one of said power switch transistors.

9. The method of claim 8, wherein said shorting comprises shorting source and drain nodes of said selected one of said power switch transistors.

10. The method of claim 7, wherein said area of high contrast is representative of a powering circuit of said given one of the distinctly powered functional blocks.

11. The method of claim 7, wherein said conductive closing comprises depositing conductive material using said ion beam.

12. A method for identifying distinctly powered functional blocks on an integrated circuit, each of the functional blocks powered via respective power interfaces of a switchable power interface on the integrated circuit, the method comprising:
identifying the respective power interfaces;
conductively closing a selected one of the respective power interfaces;
applying an external voltage bias to the switchable power interface;
imaging the integrated circuit using a focused ion beam; and
identifying an area of high contrast as representative of a given one of the distinctly powered functional blocks as being operatively powered via said selected one of the respective power interfaces.

13. The method of claim 12, wherein said identifying comprises, prior to said conductively closing:
imaging the integrated circuit using a focused ion beam; and
identifying imaged components exhibiting high contrast as representative of the respective power interfaces.

14. The method of claim 12, wherein said respective power interfaces consist of power switch transistors, and wherein said conductively closing comprises shorting a selected one of said power switch transistors.

15. The method of claim 14, wherein said shorting comprises shorting source and drain nodes of said selected one of said power switch transistors.

16. The method of claim 12, wherein said area of high contrast is representative of a powering circuit of said given one of the distinctly powered functional blocks.

17. The method of claim 12, wherein said conductive closing comprises depositing conductive material using said ion beam.

18. A method for identifying a switchable power interface on an integrated circuit, wherein the switchable power interface comprises a source and a drain with a control switch therebetween, the control switch being controllable by a control signal during operation of the integrated circuit, the method comprising:
applying an external voltage bias to a power input on the integrated circuit;
gathering an image of the integrated circuit when exposed to an ion beam; and
identifying an endpoint of an area of high contrast indicating conductive connectivity with said power input, said endpoint identifying the switchable power interface having the source and the drain.

19. The method of claim 18, wherein the method further comprises connecting, with a deposited conductive material, the source and the drain.

20. The method of claim 19, wherein the method further comprises gathering a second image of the integrated circuit after said connecting, and comparing said second image to identify areas of high contrast shown solely in said second image and thus indicative of functional componentry in operative connection with said switchable power interface.

21. The method of claim 19, wherein said deposited conductive material is deposited by said ion beam.

22. The method of claim 20, wherein said functional componentry is at least a portion of a processing core in a multi-core processor.

23. A device for identifying distinctly powered functional blocks on an integrated circuit, each of the functional blocks powered via respective power interfaces of a switchable power interface on the integrated circuit, the device comprising:
a focused ion beam emitter for directing an ion beam at a substrate;
a secondary electron detector for measuring at each of a plurality of locations on the substrate respective intensities of secondary electrons emitted from the substrate when exposed to the ion beam, each said measured intensity for generating image data indicative of features at each said respective location; and
a bias applicator for connecting an external voltage bias to a portion of the integrated circuit conductively associated with said switchable power interface;
wherein differences in regions of high contrast in respective images of said integrated circuit taken before and after shorting said switchable power interface indicate a distinctly powered functional block on said integrated circuit.

24. The device of claim 23, wherein the focused ion beam emitter is configured to deposit conductive material for shorting said switchable power interface.

25. The device of claim 24, wherein said switchable power interface is a power switch transistor.

* * * * *